United States Patent [19]
Franetzki et al.

[11] Patent Number: 5,522,695
[45] Date of Patent: Jun. 4, 1996

[54] CONTROLLABLE DENTAL TURBINE

[75] Inventors: Manfred Franetzki, Bensheim; Juergen Wohlgemuth, Darmstadt, both of Germany

[73] Assignee: Siemens Aktiengesellschaft, Munich, Germany

[21] Appl. No.: 298,294

[22] Filed: Aug. 31, 1994

Related U.S. Application Data

[62] Division of Ser. No. 985,266, Dec. 3, 1992, Pat. No. 5,364,227.

[30] Foreign Application Priority Data

Dec. 17, 1991 [DE] Germany ............... 41 41 673.2

[51] Int. Cl.⁶ ........................................... F01D 17/06
[52] U.S. Cl. ..................................... 415/35; 415/904
[58] Field of Search ........................ 415/35, 202, 904

[56] References Cited

U.S. PATENT DOCUMENTS

| | | |
|---|---|---|
| 958,120 | 5/1910 | Henry, Jr. . |
| 976,174 | 11/1910 | Henry, Jr. . |
| 1,613,950 | 1/1927 | Jackson . |
| 2,889,117 | 6/1959 | Wimpress . |
| 3,189,999 | 6/1965 | Reiter . |
| 3,270,417 | 9/1966 | Stram . |
| 3,639,074 | 2/1972 | Killick . |
| 3,865,505 | 2/1975 | Flatland . |
| 3,955,284 | 5/1976 | Balson . |
| 4,355,949 | 10/1982 | Bailey . |
| 5,066,191 | 11/1991 | Wuehrer . |
| 5,364,227 | 11/1994 | Franetzki et al. ............ 415/35 |

FOREIGN PATENT DOCUMENTS

| | | |
|---|---|---|
| 310932 | 10/1973 | Austria . |
| 0179078 | 9/1988 | European Pat. Off. . |
| 379291 | 8/1923 | Germany . |
| 810380 | 7/1949 | Germany . |
| 3105978 | 12/1981 | Germany . |
| 3702719 | 8/1988 | Germany . |

Primary Examiner—John T. Kwon
Attorney, Agent, or Firm—Hill, Steadman & Simpson

[57] ABSTRACT

A regulatable dental turbine includes an actuator arrangement which is provided for regulating the speed by varying the amount of an essentially constant volume stream of drive fluid striking a turbine wheel of the dental turbine. The change of the direction based on the actuator arrangement may bypass a portion of the volume hitting the blades of the dental turbine or may create a portion of the stream as a deceleration force acting on the turbine wheel. The actuator arrangement can operate in a speed-dependent fashion based on the flow deflected by the blades of the wheel on an impact surface or can act with a speed sensor determining the rate of rotation of the turbine wheel.

5 Claims, 8 Drawing Sheets

CONTROLLABLE DENTAL TURBINE

This is a division of application Ser. No. 07/985,266 filed Dec. 3, 1992, which issued as U.S. Pat. No. 5,364,227 on Nov. 15, 1994.

BACKGROUND OF THE INVENTION

The present invention is directed to a regulated dental turbine having an arrangement for directing a volume stream of a drive fluid onto a turbine disc or wheel and includes an arrangement for regulating the speed of the turbine wheel.

Two types of drives are principally utilized at present in order to do justice to different preparations in the dental practice. One of these drives is a turbine drive, which has extremely high no-load speeds which are 300,000 RPM. The other type of drive is an electric or air motor which has a lower speed in comparison to turbine speeds and up to a maximum of approximately 200,000 RPM.

Dental turbines have the advantage of a relatively simple structure and simple supply, but are burdened, however, by the disadvantages of a relatively low drilling power and of a high no-load speed that drops greatly when loaded by an external load or moment M. A relatively high wear and the risk of burning dental substances are also consequences of this high speed.

Although electric or, respectively, air motor drives will supply adequate torque and drilling power, the optimum speed in a range of 180,000 RPM through 200,000 RPM can only be achieved with considerable technological outlay with many rapidly moving parts, which has the consequence of a correspondingly high wear, relatively high weight and relatively high cost.

These different properties require that the dentist currently usually requires both types of drives in one treatment unit.

In order to avoid a decrease in the speed under loads given dental turbines, it has already been proposed to keep the speed constant independent of load. U.S. Pat. No. 3,865,505, whose disclosure is incorporated herein by reference thereto, discloses a controllable turbine of this type. In this patent, a valve is arranged in the delivery channel of the driving compressed air, and this valve is controlled by the volume throughput of the return air. When the speed of the turbine drops, due to the external load, then the valve in the delivery channel is opened and a larger air volume is, thus, conducted to the turbine. The control of the admission air stream, dependent on the returned air, can occur in various ways in the known turbine. Among these ways are a spring-loaded slide in the returned air channel that controls the valve in the delivery channel or can occur via a diaphragm-type barometric cell arranged in the returned air channel that adjusts a piston which controls the flow in the delivery or admission channel.

Among other things, the known turbine is effected with the disadvantage that relatively great forces are required for throttling the overall air stream. These relatively great forces are capable of being provided in the exhaust air channel only upon utilization of volume and mass. An unstable control behavior of the turbine, however, is, thus, created. In addition, the known arrangement causes a relatively large structure within the turbine handpiece, as a result whereof the integration problems can occur.

SUMMARY OF THE INVENTION

The object of the present invention is to provide a speed-regulated turbine that unites the positive properties of a turbine drive and also the positive properties of a motor drive and avoids the disadvantages of the known regulatable turbine.

To accomplish these goals, the present invention is directed to a regulatable dental turbine which includes a turbine wheel, means for supplying a constant drive fluid to the turbine wheel, and an actuator which will vary the effect of the essentially constant volume of stream of drive fluid on the turbine wheel. This variation in the effect is that the volume stream of the drive fluid is deflected at the turbine wheel in a speed-dependent fashion in terms of its effect on the impact surfaces of an actuating drive which influences the volume stream.

A critical feature of the control, according to the present invention, is that the volume stream of the drive fluid remains essentially constant so that a throttle location, which significantly influences the flow of the fluid, is present neither in the admission or inlet channel nor in the exhaust air line. Alternatively thereto, on the other hand, in combination therewith, a volume stream deflected at the turbine wheel or disc can have its action directed speed-dependently onto the impact surfaces of an actuating drive or actuator that influences the adjustment means.

Since compressed air is generally employed at present as the drive fluid, this agent shall always be addressed below, even though it lies within the framework of the invention to also employ other suitable drive agents.

The speed control can occur either self-regulating or with the assistance of a sensor via a rated/actual comparison. In this latter control, the speed n of the rotor or turbine disc is acquired with a suitable sensor and the current speed is compared in a regulator to a set rated value $n_s$. Given deviation, the regulator influences a setting means via an actuating drive, which will be set forth in greater detail later, and the setting means directs the volume stream of the driving air stream that emerges from the nozzle and impinges on the turbine wheel so that a speed deviation remains optimally constant or, respectively, extremely low up to a maximally possible load of $P_{max}$.

Regulating the speed to a rated value of the desired, optimum speed advantageously occurs in the following way:

The turbine, similar to in known instances, has a drive fluid applied to it and is placed in rotation. The driving stream is varied only in the immediate proximity of the turbine wheel or rotor disc of the turbine. This is done in the immediate proximity in order to keep dead time short and to suppress the influence of the compressibility of the air and, potentially, the elastic leads, which would lead to unstable control behavior or to delayed setting to load changes of the drill.

The influencing of the volume stream can occur by (a) variations in the stream guidance that is directed onto the turbine blades to a greater or lesser extent;

(b) a variable deceleration of the turbine blades; or (c) a combination of the versions (a) and (b).

The stream guidance can be advantageously varied with either a deflection vane, which is located between the nozzle aperture and the rotor disc or on the basis of a stream splitter in the region of the nozzle discharge opening. Another way of guidance is a relative displacement of the rotor disc relative to the nozzle aperture, either by an axial displacement of the rotor disc or by changing the nozzle's position relative to the rotor disc.

The speed measurements can occur:

(a) optically, for example by acquiring a mark on the turbine wheel;

(b) inductively, for example by measuring the voltage that is induced in an externally arranged coil by magnets secured on the turbine wheel;

(c) capacitatively, for example by measuring the change in the capacitance of a capacitor formed by the passing turbine blades and fixed cooperating electrodes; or (d) in a flow-associated fashion, for example by measuring flow changes of the driving air stream deflected at the turbine blades or buckets.

Other methods of measuring the speed which are not expressly cited here are also possible within the framework of the present invention.

As already addressed, the control can occur either indirectly, electronically in combination with electro-magnetic, piezo-electric or other actuating drives or directly, mechanically or flow-mechanically upon utilization of load-dependent forces in the drive system of the turbine or based on a combination of both of the above methods.

A regulating principle, as well as a number of design exemplary embodiments of a regulatable turbine of the present invention are described hereinbelow and other advantages and features of the invention will be readily apparent from the following description of the preferred embodiments, the drawings and claims.

BRIEF DESCRIPTION OF THE DRAWINGS

FIGS. 3–15 are a number of illustrations of embodiments of regulator turbines of the present invention, wherein the first embodiment of FIGS. 3 and 4 illustrate a magnetically-controlled deflection with FIG. 3 illustrating the deflector in a no-load situation and FIG. 4 illustrating the deflector in a maximum-load situation;

FIGS. 7 and 8 illustrating a third embodiment with FIG. 7 showing the no-load situation and FIG. 8 illustrating the maximum-load situation;

FIGS. 9 and 10 directed to a fourth embodiment of the control system with FIG. 9 showing the maximum-load situation and FIG. 10 illustrating the no-load situation; and FIGS. 11, 12 and 13 showing a fifth embodiment of the regulating turbine with FIG. 11 illustrating a no-load situation;

FIG. 12 illustrating a maximum-load situation and

FIGS. 14 and 15 illustrating a sixth embodiment of the self-regulating turbine with FIG. 14 illustrating the no-load situation and FIG. 15 illustrating the maximum-load situation.

DESCRIPTION OF THE PREFERRED EMBODIMENTS

The principles of the present invention can be incorporated in a regulating arrangement for an indirect regulation of the speed upon involvement of a sensor and of a regulator having rated/actual value comparison.

Figure 1:
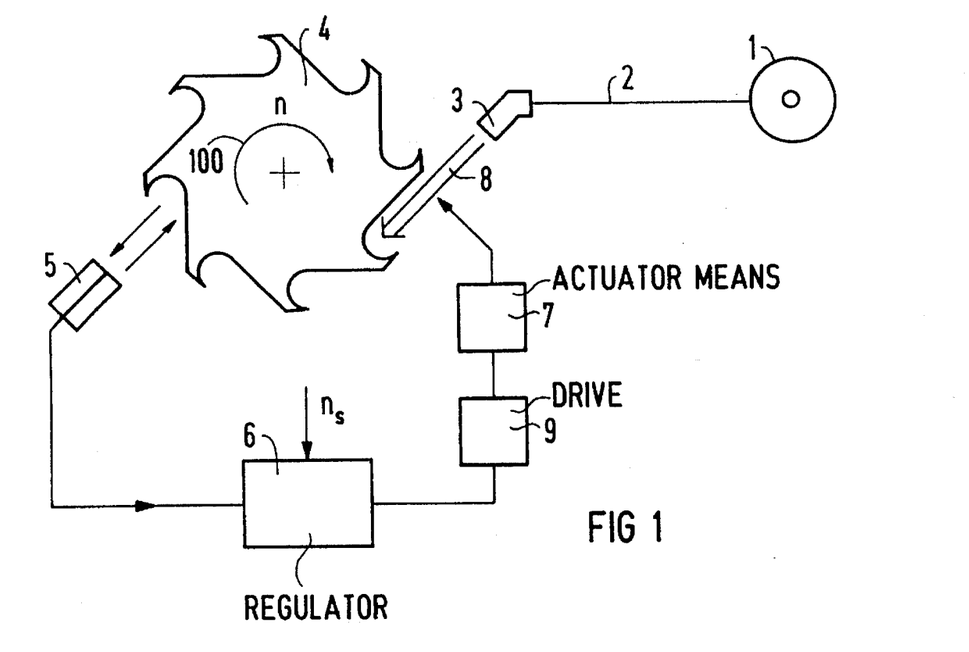
FIG. 1 is a schematic illustration of a regulating principle for regulating the speed of a turbine drive in accordance with the present invention.

A dental turbine handpiece (not illustrated) is constructed in a known way and will contain a turbine that is driven with a suitable fluid from a supply source 1 via a line 2. Since compressed air is the drive agent usually employed at present, this shall always form the basis below. It is conceivable and also within the framework of the present invention, however, to employ some other suitable drive agent. The air supplied by the line 2 is passed through a nozzle 3 directly charging the blades or buckets of a turbine rotor, disc or wheel 4 in a known way to rotate the turbine in the direction of arrow 100.

In the regulated turbine of the present invention, the speed of the rotor disc or turbine wheel 4 is acquired with a suitable sensor 5. The current speed is compared to an adjustable rated value $n_s$ in a regulator 6. Upon deviation, the regulator 6 activates an actuating drive 9 for actuating means 7, which will be set forth in greater detail in the following exemplary embodiments. The actuating means 7 will influence the driving air stream, which is a volume stream, as indicated by the arrow 8, and will direct this stream onto the rotor disc, mainly so that the speed variation remains as small as possible up to a maximum load $P_{max}$. Expediently, the rated value that has been set lies at the optimum operating speed of the turbine. Actuating means 7, of which a number of advantageous embodiments are presented hereinbelow, makes it possible to keep the speed approximately constant over a relatively great range of loads.

Figure 2:
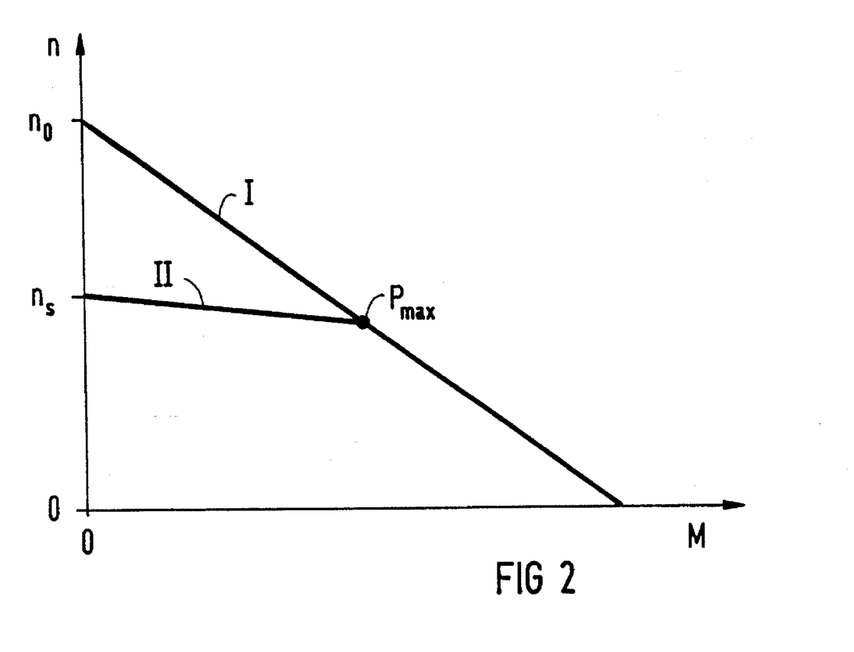
FIG. 2 is a graph illustrating the characteristic control behavior of the invention compared to the prior art control.

With reference to the speed control, the line 1 in FIG. 2 illustrates the change of speed as the load M increases for a prior art turbine. In FIG. 2, the line II is the speed of the regulated turbine of the present invention. Between a no-load situation to a load $P_{max}$, the speed variation is very small in the present invention; however, it has a sharp drop off in the prior art devices.

Exemplary Embodiment 1

Figure 3:
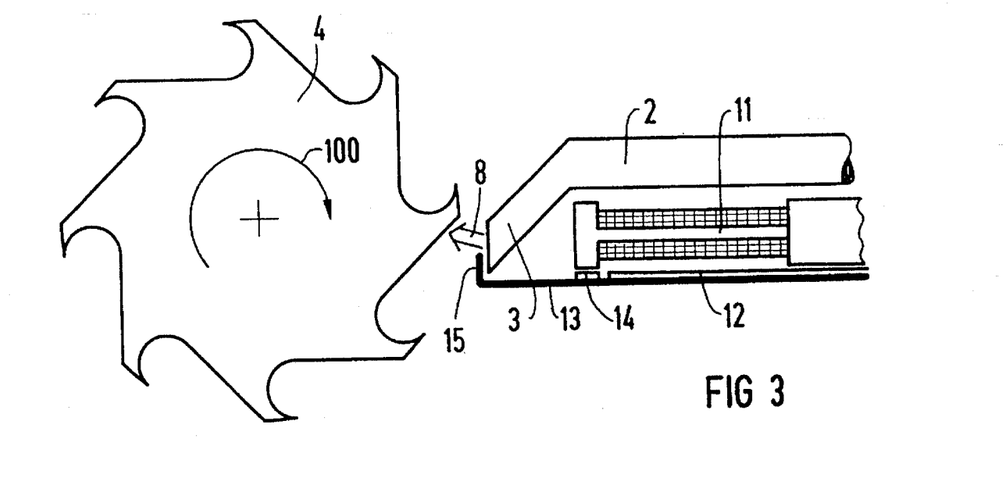

In order to set a no-load speed, as desired, the effect of the air stream 8 from the nozzle 3 at the device illustrated in FIG. 3 onto the turbine or rotor disc 4 can be influenced by an electro-magnetic system composed of a magnetic coil 10 with a soft iron core 11 and a soft iron return 12. An armature plate 14 is mounted on a flexural stem or spring 13 and the spring has an angled-off section or vane 15, which can be introduced between the nozzle aperture of the nozzle 3 and the turbine disk 4.

As illustrated in FIG. 3, one final position of the deflection vane 15, given a fully activated coil, is for a desired no-load speed. In this position, the vane 15 partially occludes the nozzle aperture 3 and deflects the emerging air stream 8 so that only a portion engages the buckets or blades of the rotor or turbine 4.

Figure 4:
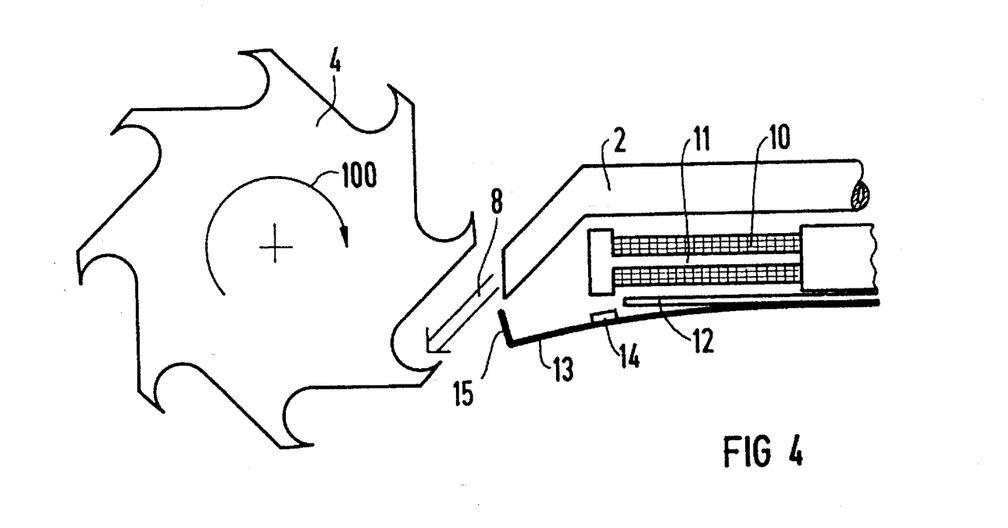

FIG. 4 shows the other final position of the deflection vane 15, which is for a maximal load $P_{max}$ of the turbine 3. The coil current is completely shut off. Due to the spring power of the flexural spring 13, the deflection vane 15 is completely retracted from the nozzle aperture so that the direct flow 8 strikes the buckets or blades of the turbine wheel so that the drive stream is optimum in this case for the maximum efficiency.

Various coil drives can be selected for the speed regulations between a no-load and maximum load $P_{max}$. Advantageously, thus, the deflection vane 15 can be pulled in front of the nozzle aperture to a greater or lesser extent in an analog fashion via a variable coil current opposite the restoring force of the spring 13. Alternatively, it is conceivable to move the deflection vane 15 back and forth between the desired two final positions in a digital fashion with a fixed clock frequency, for example at 200 Hz. Regulation can, therefore, occur by varying the clock frequency.

Exemplary Embodiment 2

Similar to Embodiment 1, the stream guidance is likewise influenced by a deflection vane 15 in this embodiment. Differing from Embodiment 1, however, the portion of the air stream 8 that strikes the rotor disc or turbine 4 is varied here. Whereas only the portion 8a is effectively directed onto the blades of the turbine in the one final version illustrated in FIG. 5, that corresponds to the desired, no-load speed. The remaining portion 8b, by contrast, is largely unutilized. The full air stream impinging on the turbine blades or buckets in the other Figure (FIG. 6) corresponds to the speed given a maximum load.

Figure 5:
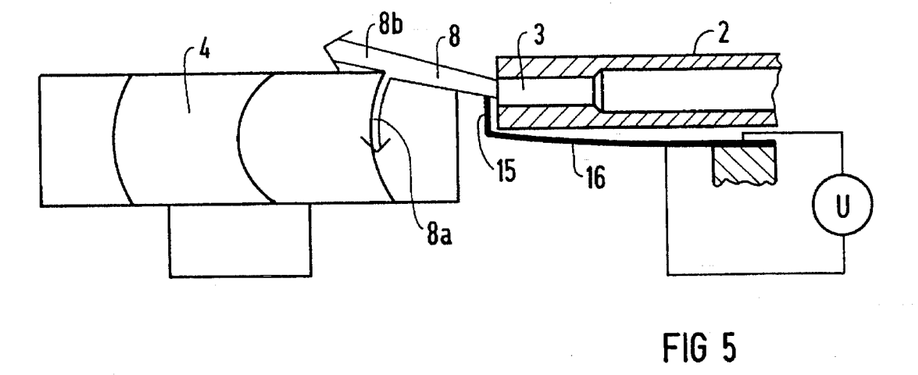
FIGS. 5 and 6 showing a different modification of a deflector device with FIG. 5 illustrating the device with a no-load situation and FIG. 6 showing the arrangement in a maximum-load situation.
Figure 6:
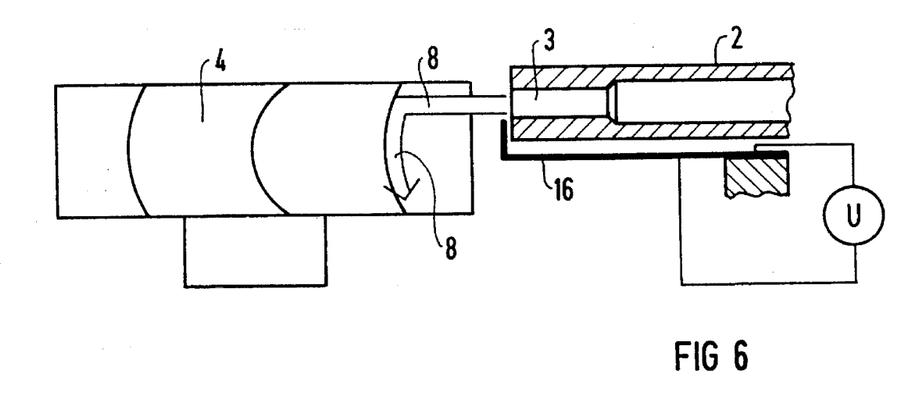

A piezo-electric flex bar 16 is employed as the actuating drive for the deflection vane 15. This flex bar 16 bending under the influence of an applied electrical voltage U so that a position of the deflection vane 15 in the air stream is varied. The drive voltage U can be varied in an analog or digital fashion like the coil current in Embodiment 1 between the two final positions for no-load and full-load position.

Exemplary Embodiment 3

Figure 7:
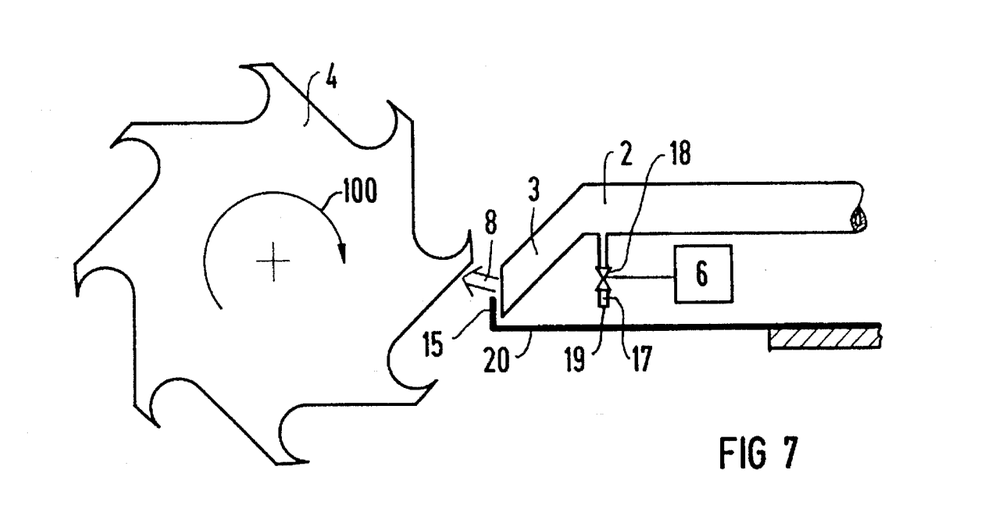
Figure 8:
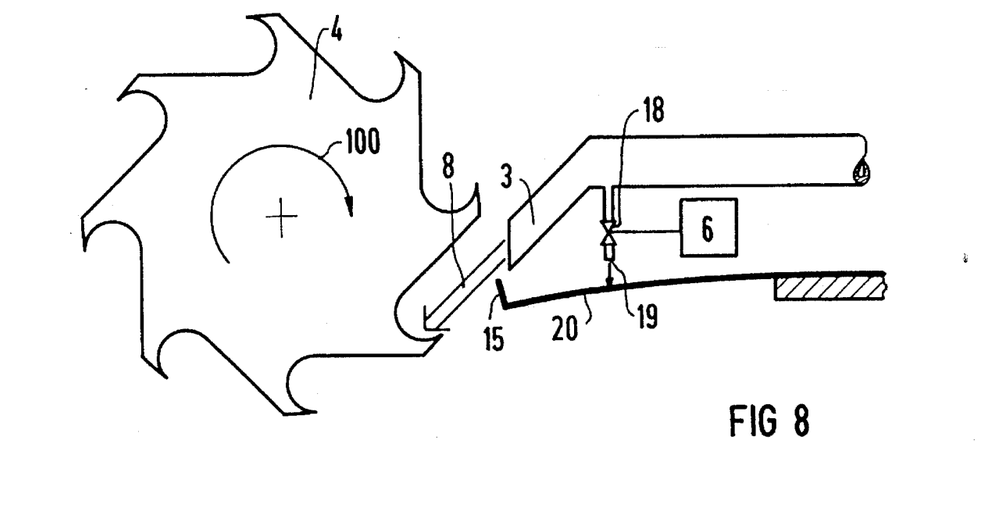

This exemplary embodiment discloses the possibility of reducing the space required for the electrical drive control elements that are required in the turbine handpiece. In this example, a branch line 17 extends or branches off of the admission line 2 and has a valve 18 which is arranged in the line to form the actuating drive. A discharge nozzle 19 of this branch line 17 is directed onto a leaf spring 20.

The air stream from the discharge nozzle 3 is influenced by the deflection vane 15 which is secured to the leaf spring 20, similar to the way as set forth with regard to Embodiment 1. The valve 18 can expediently be a solenoid valve that is activated by the regulator 6 according to FIG. 1.

Whereas the nozzle 19 in FIG. 7 is closed by the valve 18 to form the no-load position, in FIG. 8, the valve 18 is opened to form the maximum load position. The air stream flowing from the nozzle 19 will press the leaf spring 20 and, thus, move the deflection vane 15 out of the air stream of the discharge nozzle 3. Since the auxiliary air stream required and, thus, the cross section of the auxiliary nozzle is relatively small, the required solenoid valve 18 can also be kept correspondingly small.

Analogous to Embodiments 1 and 2, as set forth above, the auxiliary air stream, however, can also be influenced with an electro-magnetic or a piezo-electric actuated drive having deflection vanes between the auxiliary nozzle opening and the leaf spring.

Exemplary Embodiment 4

Figure 9:
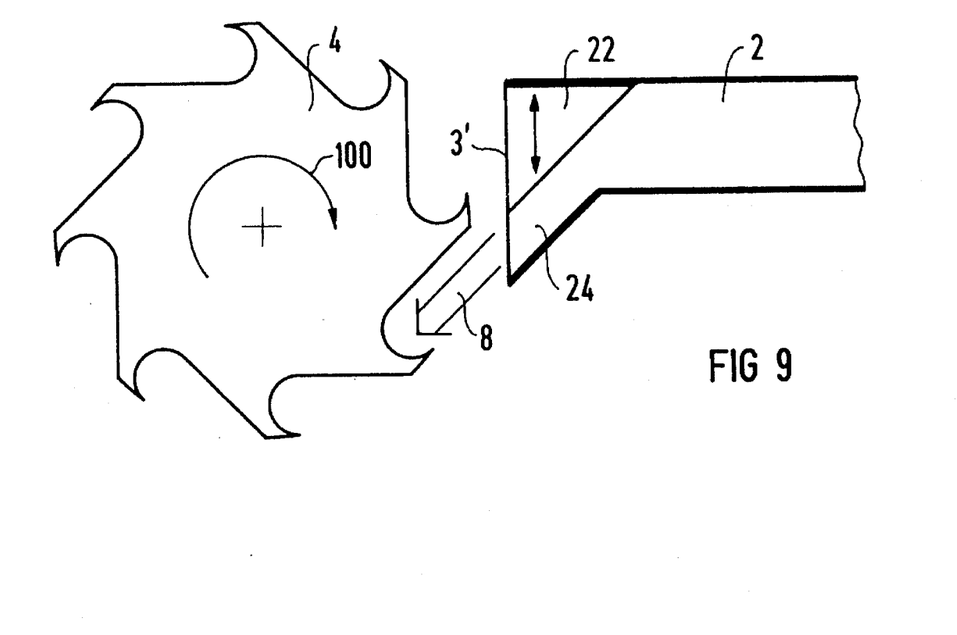
Figure 10:
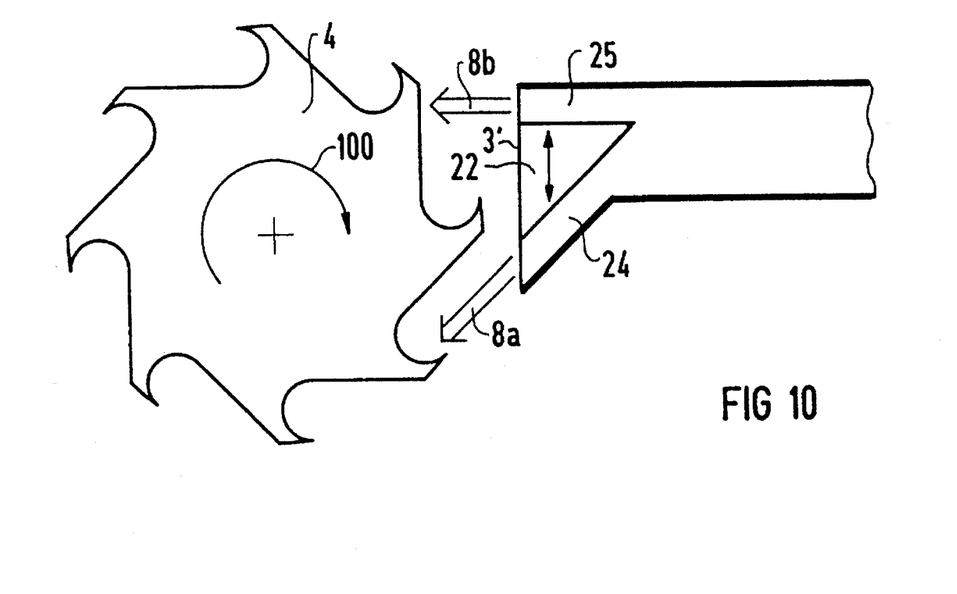

In this embodiment, a flow divider 22 is provided in the air discharge nozzle 3'. Using the flow divider 22, the cross section of the discharge nozzle aperture can be varied so that either the entire volume stream 8 is conducted through the discharge nozzle 24, as illustrated in FIG. 9, for a full-load condition, or the volume stream 8 is subdivided into variable sub-streams 8a and 8b, whereas one of the sub-streams 8a acts as a drive stream passing through the nozzle 24 of reduced size. The other sub-stream 8b emerges via a nozzle aperture 25, which is formed upon the adjustment, and acts as a decelerating stream, as illustrated in FIG. 10.

FIG. 9 shows the flow divider 22 movable for varying the cross section of the nozzle apertures 24 and 25 in one final position wherein the drive nozzle 24 has the maximally possible cross section. The deceleration nozzle 25, in contrast, is entirely closed. This is the position for a full load $P_{max}$. FIG. 10 shows the flow divider 22 in the other final position, which is a no-load position. The drive nozzle cross section 24 is reduced here and the deceleration nozzle 25, by contrast, is open.

The systems described in Embodiments 1–3 can be provided as actuating drives for the flow divider 22. It should be noted that, as illustrated, the flow 8b opposes rotation of the rotor 4 in the direction illustrated by the arrow 100. Thus, the flow 8b is shown here as a deceleration flow similar to the arrangement in FIG. 3, wherein a portion of the flow acts to oppose rotation in the direction of arrow 100.

Exemplary Embodiment 5

Figure 11:
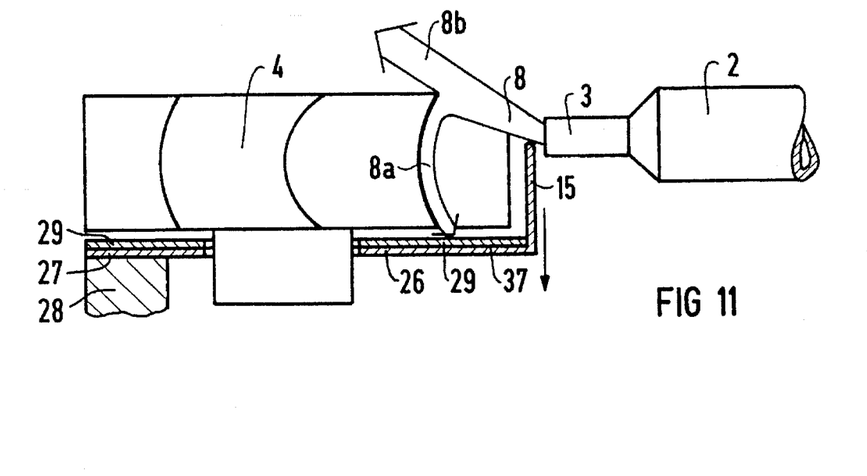

This exemplary embodiment shows a possible embodiment for self-regulating turbine. The deflection vane 15 acts as an actuator for varying the effect of the volume stream and is situated on an annular flexural spring 26. The spring 26 is concentrically arranged under the rotor disc 4 and is mounted on a carrier 28 so that it serves as an actuating drive for the deflecting vane 15.

As illustrated in FIG. 11, the air stream 8 is deflected by the deflecting vane 15 to be sub-divided into partial air streams 8a and 8b. In a no-load position illustrated in this Figure, the rotor disc or turbine wheel 4 offers no noteworthy flow resistance and rotates freely with the flow 8a that is still impinging on its blades or buckets. As in Embodiment 3, the no-load speed is reduced to the desired extent by engagement of the deflecting vane 15 into the stream guidance of the driving air.

When the rotor disc is decelerated by an external moment or load, the flow resistance at the rotor disc blades is, thus, increased and the air stream will be deflected at the surfaces of the buckets or blades. The deflected air will impinge on an impact surface 37 of the flexural spring 26 and cause the spring to be deflected downward to withdraw the deflecting vane 15 from the driving air stream.

Figure 12:
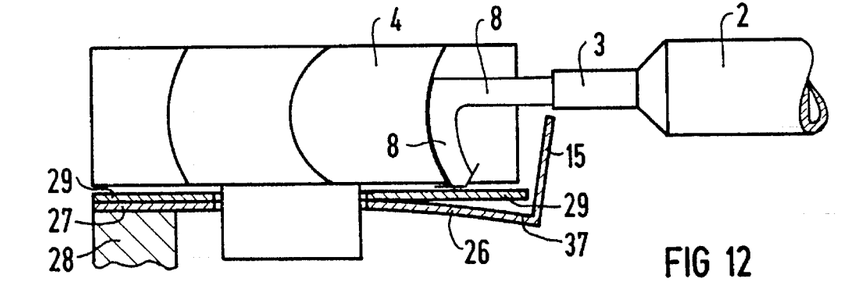

The force of the deflected air onto the flexural spring 26 is all the higher and the deflecting vane 15 is pulled farther and farther from the driving air stream with the greater decelerating moment of the turbine. FIG. 12, again, shows the final position with the full load $P_{max}$. The driving air jet 3 is completely free here, as a result whereof the drive stream 8 is optimally directed onto the turbine wheel or disc 4.

For influencing, particularly for improving the control characteristics, the characteristics and/or spring characteristics of the above-mentioned flexural spring can be varied. The characteristics can, thereby, be varied by appropriate shaping of the stream deflecting part or of the nozzle discharge opening, as well. The nozzle aperture, for example, can be given a cross section deviating from a circular cross section. In order to suppress hunting, the flexural spring can also be coupled to a suitable dampening element.

Figure 13:
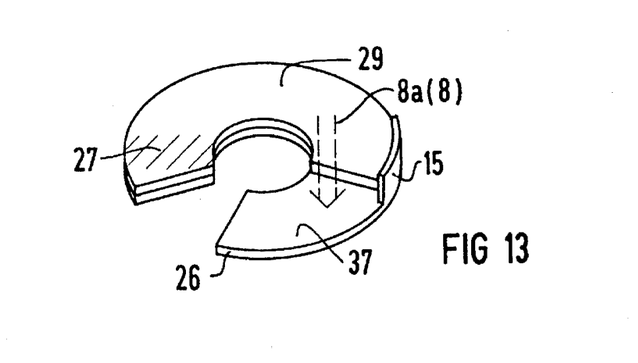
FIG. 13 being a perspective view of a flexural spring utilized in the embodiment.

FIG. 13 shows one possibility for the design of the flexural spring 26. In this design, the spring 26 forms only a portion of an annulus and has only the shaded region referenced 27 clamped to a correspondingly fashioned carrier 28, which may be part of the turbine housing. In order to improve the control characteristics, a dividing plate 29 can be arranged between the turbine wheel 4 and the spring 26. Such a dividing plate serves as a shield against a suction effect between the turbine wheel and the spring 26, which will potentially occur in this region.

For varying the spring characteristics, the flexural spring 26 can be provided with a dampening element in that, for example, an oscillation-attenuating foil or the like is applied on the spring.

Disengaged from the embodiments set forth up to now wherein the volume spring for the speed regulating event remains practically constant, the principle set forth with reference to Exemplary Embodiment 5, namely to steer the air stream deflected at the rotor disc onto the impact surface of an actuating drive or actuator with an effect dependent on speed, offers the possibility of controlling the volume stream with, for example, a throttle or the like arranged in the delivery line.

Exemplary Embodiment 6

The sixth embodiment is a self-regulating turbine. In this embodiment, the rotor disc or turbine wheel 4 is mounted for free mobility on the shaft 30. The motion play is limited by an oblique channel 31 in a rotor disc collar 131 and by a dog peg 32, which is received in a channel and rigidly connected to the shaft 30. A Belleville spring washer 33 is concentrically arranged on the shaft 30 between a shaft collar 34 and the rotor disc 4 to urge the disc 4 axially on the shaft 30 in the downward direction, as illustrated in FIGS. 14 and 15.

Figure 14:
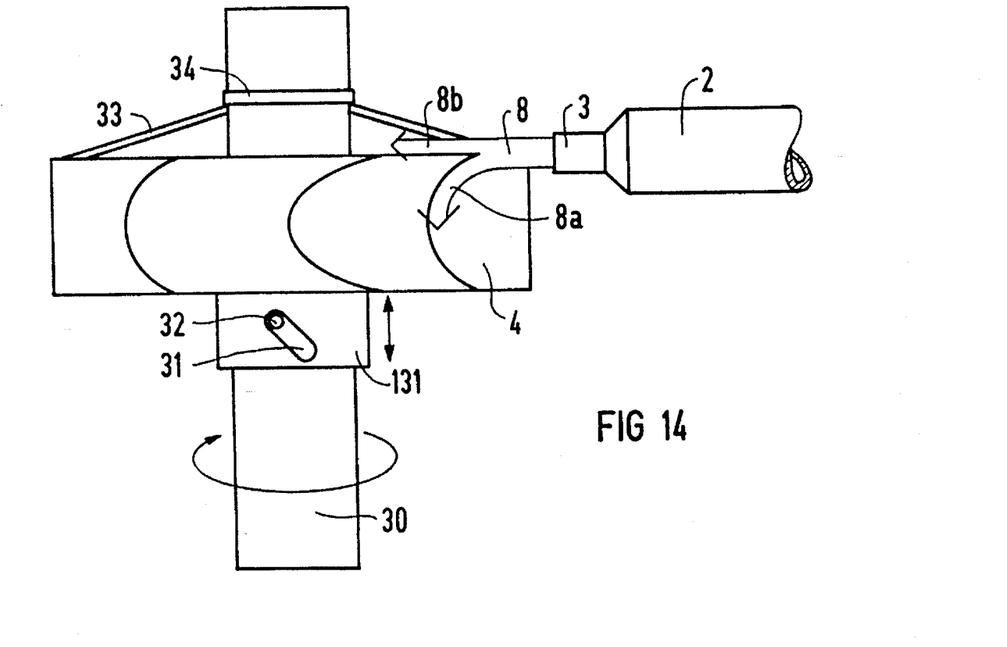

FIG. 14 shows the rotor disc as it is pressed to its lowest final position by the spring 33, and this position is a no-load position. As a result of this position, the driving air stream 8 from the nozzle 30 is divided into partial streams 8a and 8b, wherein the partial stream 8b flows off over the rotor disc 4 without any effect. In no-load, the blades of the rotor disc 4 offer no flow resistance and rotate freely with the remaining instant air stream 8a at a reduced speed.

Figure 15:
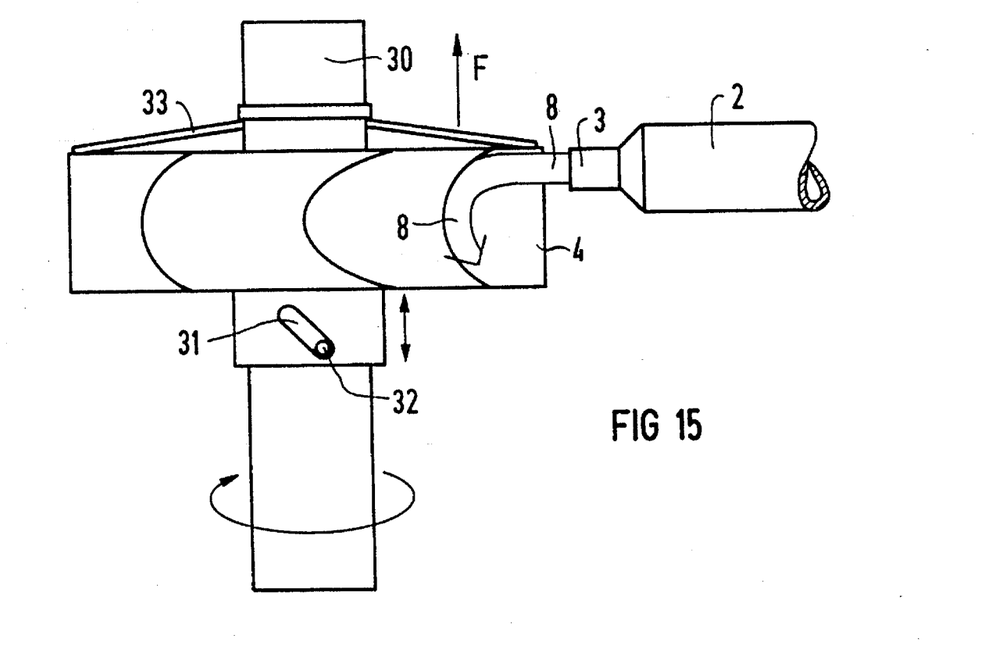

FIG. 15 shows the rotor disc 4 positioned when a maximum load $P_{max}$ is applied to the drive shaft. The blades or buckets of the rotor disc 4, here, are charged with the full driving air stream 8.

When the shaft 30 is decelerated by an external torque, then this movement is transmitted via the dog peg 32 in the shaft and the oblique channel 31 in the rotor disc collar to the rotor disc 4 by the slanting channel 31. The rotor disc is thereby pressed up against the force of the spring 33. The area over which the air stream attacks the buckets or blades of the rotor disc is, thus, enlarged and the decelerating moment is compensated by an increased drive moment from an increased amount of air striking the blades.

When decelerating the rotor disc 4, in addition, the flow resistance in the rotor blades is increased and the air stream is deflected downwardly by the curved blades. An upwardly directed reaction force F which promotes the above-described displacement of the rotor disc 4 in an upward direction will occur as the upper blade halves are impinged by the air stream.

Exemplary Embodiment 7

Figure 16:
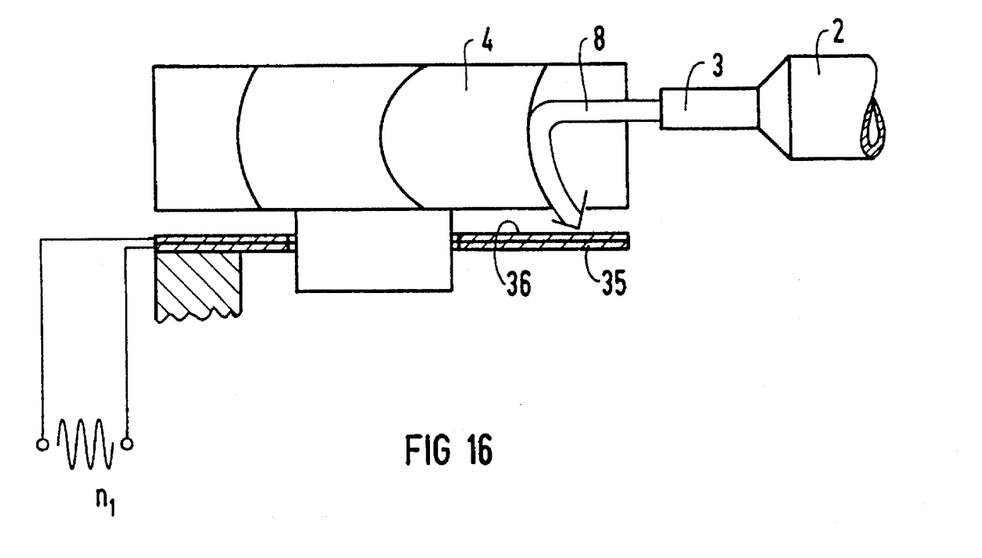
FIG. 16 illustrates an embodiment of a sensor for acquiring the turbine speed in accordance with the present invention.

Exemplary Embodiment 7 is illustrated in FIG. 16 and shows a version of a sensor for acquiring the turbine speed which is well-suited for the last-described embodiments.

In this version, an annular, piezo-electric flex element 35 is arranged under the rotor disc 4 concentrically with the axis of the rotor disc 4. The driving air stream 8 or, respectively, the sub-stream 8a will impinge on an impact surface 36 of the flex element 35 after flowing through the rotor disc blades and will generate an electrical pulse. The pulse sequence having the frequency $n_1$, which thus occurs, is directly proportional to the turbine speed n according to the relationship $$n_1 = Nn$$

wherein N is the number of turbine blades for the rotor 4. This turbine speed can then be determined in an extremely simple manner with such a sensor.

Although various minor modifications may be suggested by those versed in the art, it should be understood that we wish to embody within the scope of the patent granted hereon all such modifications as reasonably and properly come within the scope of our contribution to the art.

We claim:

1. A regulatable dental turbine comprising a turbine wheel, a nozzle for a drive fluid being directed at said turbine wheel on a shaft, said nozzle providing essentially a constant volume stream, and actuator means for regulating the speed of the turbine wheel acting to vary the effectiveness of the essentially constant volume stream engaging the turbine wheel, the actuator means changing the position of the turbine wheel in an axial direction on the shaft relative to the discharge nozzle.

2. A regulatable dental turbine according to claim 1, wherein the actuator means automatically varies the position of the turbine wheel, dependent on the load applied to the drive shaft of the wheel.

3. A regulatable dental turbine according to claim 2, wherein the turbine wheel includes blade surfaces obliquely oriented relative to the stream direction leaving the discharge nozzle to create an axially-acting actuating force for shifting the turbine wheel on the shaft in a first direction in addition to rotating the wheel in a running direction on said shaft, said actuating force varying the position of the turbine wheel relative to the discharge nozzle in a load-dependent fashion, said actuator means including a spring element moving the turbine wheel on the shaft in a direction opposite to said actuating force so that as the load on said shaft increases, the wheel moves axially against said spring element to increase the amount of the flow from the discharge nozzle acting on said blades of said turbine wheel.

4. A regulatable dental turbine according to claim 2, wherein the actuator means automatically adjusts the position of the turbine wheel on the drive shaft in response to load changes of the drive system utilizing the direct torque transmitted from the wheel onto the shaft to position the wheel in the drive stream against an elastic acting adjustment force positioned between the turbine wheel and shaft.

5. A regulatable dental turbine according to claim 4, wherein the elastically acting adjustment mechanism between the turbine wheel and shaft is formed by a guide surface of the shaft acting on a corresponding guide surface of the turbine wheel, at least one of said guide surfaces being a helical surface, said movement of said pair of guide surfaces being limited by a detente and being opposed by a spring element acting on the turbine wheel to move the wheel in a direction opposite to the force created by the torque.

* * * * *